United States Patent
Narayanan et al.

(10) Patent No.: US 6,506,396 B1
(45) Date of Patent: *Jan. 14, 2003

(54) STABLE MEDICATED ANIMAL CARE FORMULATION

(75) Inventors: Kolazi S. Narayanan, Wayne, NJ (US); Domingo I. Jon, New York, NY (US); Donald I. Prettypaul, Englewood, NJ (US)

(73) Assignee: ISP Investments Inc., Wilmington, DE (US)

( * ) Notice: Subject to any disclaimer, the term of this patent is extended or adjusted under 35 U.S.C. 154(b) by 31 days.

This patent is subject to a terminal disclaimer.

(21) Appl. No.: 09/947,802

(22) Filed: Sep. 6, 2001

(51) Int. Cl.$^7$ .............................................. A01N 25/02

(52) U.S. Cl. ..................... 424/405; 424/406; 514/66; 514/531; 514/572; 514/937; 514/941; 514/943

(58) Field of Search .................... 514/383, 66, 531, 514/572, 937, 941, 943; 424/405, 406

(56) References Cited

U.S. PATENT DOCUMENTS 6,045,816 A * 4/2000 Narayanan et al. ......... 424/405

\* cited by examiner

*Primary Examiner*—Alton Pryor
(74) *Attorney, Agent, or Firm*—Walter Katz; William J. Davis; Marilyn J. Maue

(57) ABSTRACT

A stable medicated animal care formulation including, by weight;
  (a) 0.1–10% of an active agricultural ingredient, of an animal care and/or veterinary reagents,
  (b) 0.0002–40% of a microemulsion concentrate including:
    (i) 0–10% of a castor oil ethoxylate or tristyryl phenol ethoxylate,
    (ii) 0–1% of an ethoxylated phosphoric acid as pH buffer,
    (iii) 0.0002–4% of a N—$C_8$–$C_{18}$ alkyl pyrrolidone and
    (iv) 0–6% of a N—$C_1$–$C_4$ alkyl pyrrolidone,
  (c) a surfactant with shampoo properties, and
  (d) water, wherein (c)+(d) is 50–99.4%.

2 Claims, No Drawings

STABLE MEDICATED ANIMAL CARE FORMULATION

BACKGROUND OF THE INVENTION

1. Field of the Invention

This invention relates to animal care formulations, and, more particularly, to a stable medicated shampoo formulation for treating animals to control parasites thereon.

2. Description of the Prior Art

K. Narayanan, in U.S. Pat. No. 6,045,816, described a water-based microemulsion of an active pyrethroid insecticide for delivery of the active at a high loading to treat fruits and vegetables. The disclosure in this patent is hereby incorporated by reference herein. In this invention, there is provided a stable medicated shampoo formulation including the Narayanan microemulsion matrix, or a modified matrix thereof, for controlling parasites on animals.

SUMMARY OF THE INVENTION

What is described herein is a stable medicated animal care formulation which includes, by weight;

(a) 0.1–10% of an active agricultural ingredient, of an animal care and/or veterinary reagents, (b) 0.0002–40% of a microemulsion concentrate including (i) 0–10% of a castor oil ethoxylate or tristyrl phenol ethoxylate, (ii) 0–1% of an ethoxylated phosphoric acid as pH buffer, (iii) 0.0002–4% of a N—$C_8$–$C_8$–$C_{18}$ alkyl pyrrolidone and (iv) 0–6% of a N—$C_1$–$C_4$ alkyl pyrrolidone, (c) a surfactant with shampoo properties, and (d) water.

In a preferred form of the invention, (a) is an insecticide, most preferably, permethrin, deltamethrin, D-allethrin, piperonyl butoxide, bioresmethrin, penconozole, a mixture of D-allethrin/piperonyl butoxide, or a mixture of D-allethrin/ permethrin/ tetramethrinlipiperonyl butoxide.

Preferably, too, the total amount of (c) and (d) in the formulation is 50–99.4%, and (b) (iii) is N-octyl or N-dodecyl pyrrolidone and (b) (iv) is N-methyl pyrrolidone.

DETAILED DESCRIPTION OF THE INVENTION

In this invention, the microemulsion matrix in Narayanan, referred to hereinafter as MICROFLEX-1, or a modified form thereof, is present in a medicated shampoo formulation containing an active agricultural ingredient, such as an insecticide, e.g. a pyrethroid, for treating an animal suspected of having a parasite thereon.

The formulation, by weight is as follows:

(a) active agricultural ingredient, 0.1–10%;

(b) MICROFLEX-1, 0.00002–40%;

(i) castor oil ethoxylate or tristyryl phenol, 0–10%, (ii) ethoxylate phosphoric acid, 0–1%, (iii) N—$C_8$–$C_{18}$ alkyl pyrrolidone 0.0002–4%, and (iv) N—$C_1$–$C_4$ alkyl pyrrolidone 0–6%.

(c) surfactant with shampoo properties, e.g. anionic surfactant;

(d) water, wherein (c)+(d), 50–99.4%.

Preferably, both (b) (ii) and (iv) are present, (b) (iii) is octyl pyrrolidone or dodecyl pyrrolidone, and (b) (iv) is methyl pyrrolidone. In the modified MICROFLEX-1 matrix, essentially only (b) (iii) is present and it is preferably N-dodecyl pyrrolidone.

Generally, the agriculturally active ingredient used herein is an insecticide, preferably a pyrethroid, which is a class of well-known and widely-used insecticide of which cypermethrin, o-allethrin, permethrin, piperonyl butoxide and tetramethrin are representative examples.

The shampoo portion of the formulation includes a surfactant having shampoo properties. A typical formulation is as follows, in weight %.

| Shampoo Formulation A | Weight % |
| --- | --- |
| Sodium Laureth 2 sulfate | 9.20 |
| Cocamidopropyl-betaine | 5.10 |
| Cocamide DEA | 4.05 |
| Deionized Water | 81.45 |
| Citric Acid (25%) | 0.20 |
| Total | 100.00 |

Procedure

Dissolve sodium laureth sulfate in water
Heat the solution to 65° C.
Add Cocamidopropylbetain and Cocamide DEA
Stir the mixture until the solution is homogeneous
Cool to 45° C.
Add citric acid solution to the mixture and stir
Cool to room temperature
A clear, viscous liquid is formed.
[Shampoo Viscosity (LUT/4 sp 12 rpm/min) 7500 cps]

EXAMPLE 1

Add 1.0 g permethrin to 5.0 g Microflex-1 (Solution A) and mix in a rotary wheel for 10 minutes. Add 6 g of Solution A to 94 g of shampoo formulation A and mix the sample in a rotary wheel for 5 minutes.

The permethrin-shampoo mixture is a clear and homogeneous solution which is stable for at least 3 months.

EXAMPLE 2

| Shampoo Formulation B | |
| --- | --- |
| Sodium Laureth 2 sulfate (26%) | 35 |
| Cocamidopropyl-betaine | 5 |
| Agsol Ex-12 | 1 |
| Deionized Water | 59 |
| | 100 |

Add 1.0 g permethrin to 9.0 g Microflex-1 (Solution B) and mix in a rotary wheel for 10 minutes. Add 10 g of Solution B to 90 g of shampoo formulation A and mix the sample in a rotary wheel for 5 minutes.

The permethrin-shampoo mixture is a clear and homogeneous solution stable for at least 3 months.

EXAMPLE 3

N-dodecyl pyrrolidone (Agsol EX-12) was used to dissolve permethrin (pyrethroids) in a shampoo formulation to form a stable medicated shampoo with insecticide properties. Accordingly, 1 g of permethrin was added to 94 g of shampoo (formulation B) along with 5 g Agsol EX-12. The sample was mixed until the pyrethroid was thoroughly dispersed forming a slightly cloudy shampoo which was stable for more than 7 days.

While the invention has been described with particular reference to certain embodiments thereof, it will be understood that changes and modifications may be made which are within the skill of the art. Accordingly, it is intended to be bound only by the following claims, in which:

What is claimed is:

1. A stable medicated animal care formulation consisting essentially of, by weight;

(a) 0.1–10% of an active agricultural ingredient, of an animal care and/or veterinary reagents, selected from the group consisting of permethrin, deltamethrin, D-allethrin, piperonyl butoxide, bioresmethrin, penconozole, a mixture of D-allethrin/piperonyl butoxide, or a mixture of D-allethrin/permethrin/tetramethrin/ipiperonyl butoxide, and mixtures thereof, (b) 0.0002–40% of a microemulsion concentrate consisting essentially of (i) 0–10% of a castor oil ethoxylate or tristyryl phenol ethoxylate, (ii) 0–1% of an ethoxylated phosphoric acid as pH buffer, (iii) 0.0002–4% of a N—$C_8$–$C_{18}$ alkyl pyrrolidone and (iv) 0–6% of a N—$C_1$–$C_4$ alkyl pyrrolidone, (c) sodium laureth-2-sulfate, and (d) water, wherein (c) and (d) is 50–99.4%.

2. A formulation according to claim 1 wherein (b) (iii) is N-octyl or N-dodecyl pyrrolidone and (b) (iv) is N-methyl pyrrolidone.

* * * * *